United States Patent [19]

Drewlow

[11] Patent Number: Plant 6,389

[45] Date of Patent: Nov. 15, 1988

[54] IMPATIENS PLANT NAMED SUNREGAL

[75] Inventor: Lyndon W. Drewlow, Ashtabula, Ohio

[73] Assignee: Mikkelsens, Inc., Ashtabula, Ohio

[21] Appl. No.: 916,562

[22] Filed: Oct. 8, 1986

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Schwartz, Jeffery, Schwaab, Mack, Blumenthal & Evans

[57] ABSTRACT

An Impatiens plant named Sunregal, having lavender purple bicolor flowers; deep red-purple main stem; compact self-branching growth habit; small dark green and shiny leaves with a purple midrib, and having the ability to produce two flowers per each leaf axil thereby making it highly floriferous.

2 Drawing Sheets

The present invention relates to a new and distinctive cultivar of Impatiens plant, botanically known as Impatiens, and referred to by the cultivar name Sunregal. Sunregal was developed by me through controlled breeding by crossing the cultivar Sunglow, Mikkelsen Seedling No. 84-1133-1, (seed parent) with Mikkelsen Seedling No. 83-803-1 (pollen parent). Asexual reproduction of the progeny of the stated cross by terminal or stem cuttings performed in Ashtabula, Ohio has shown that unique features of this new impatiens are stabilized and are reproduced true to type in successive propagations.

The following characteristics in combination distinguish the new impatiens from both its parent varieties and other cultivated impatiens of this type known and used in the floriculture industry. In certain instances the characteristics are compared with similar characteristics of other cultivars. Of the cultivars referred to, Astro is disclosed in U.S. Plant Pat. No. 4,691, and Sunglow, Sunburst, Sundazzle and Twilight are disclosed in pending applications.

1. Sunregal has a distinct and very attractive purple and lavender purple bicolor flower which is similar in pattern to Sunglow, Sundazzle, and Sunburst. Twilight is only faintly bicolored and Astro is only bicolored on the upper petal.

2. Sunregal has the deepest red-purple main stem of the cultivars referred to, with Twilight having the next reddest stem; Sunglow, Sunburst and Astro being medium red, and Sundazzle being mainly green with a touch of red.

3. Flower size of Sunregal is smaller than Astro, similar to Twilight and a little larger than Sunburst, Sunglow and Sundazzle.

4. Sunregal is larger in plant size and not as mounded as Sundazzle and Sunburst, similar in size to Sunglow but not as mounded, and smaller than Astro and Twilight and not as open and upright in plant habit.

5. Sunregal has no variegation on its leaf, being similar in this respect to Sundazzle. Sunburst has a very small amount of variegation, while Astro, Twilight and Sunglow are heavily variegated.

6. Sunregal has small leaves similar to Sunglow. Astro, Twilight, Sundazzle and Sunburst all have larger leaves.

7. There is no existing cultivar with exactly the same shiny dark green leaves that Sunregal has. Sunregal also has a purple midrib which contrasts well with the bicolored flowers. Twilight and Sunglow have a more dull green leaf. Astro has more purple in the green, and Sundazzle and Sunburst are more yellow-green with purple tint.

8. Sunregal has two flowers per leaf axil, similar to Sundazzle, Sunglow and Sunburst, while Astro and Twilight only have one flower per leaf axil.

9. Sunregal is highly self-branched and vigorous, making it suitable for 4" pots, hanging baskets and bedding plant use.

10. Flowering of Sunregal is 6 to 10 days earlier than Astro and Twilight, 2 to 5 days earlier than Sunglow, and similar to Sundazzle and Sunburst.

In the accompanying colored photographs, sheet 1 illustrates the overall appearance of Sunregal, showing colors as true as it is reasonably possible to obtain in a colored reproduction of this type. Sheet 2 is an enlarged color photograph showing the shape and color of the flower in greater detail.

The following is a detailed description of my new impatiens cultivar based on plants produced under commercial practices in Ashtabua, Ohio under both greenhouse and outdoor conditions. The photographs were taken in early June of greenhouse grown plants. Color references are made to The Royal Horticultural Society Colour Chart except where general terms of ordinary dictionary significance are used.

Parentage: A controlled cross between Mikkelsen Seedling No. 84-1133-1 (Sunglow) and Mikkelsen Seedling No. 83-803-1.

Propagation:

(A) *Type cutting.*—Stem 15 mm long will develop to 4 to 5 cm long in 18 to 21 days.

(B) *Time to root.*—8 to 10 days at 23° C. summer, and 10 to 12 days at 20° C. winter.

(C) *Rooting habit.*—Heavy, fibrous.

Plant description:

(A) *Form.*—Compact, symmetrically mounded, self-branching, red purple stemmed, vigorous growing flowering herb.

(B) *Habit of growth.*—Vigorous, self-branching, compact, mounded, continuous flowering once it has started.

(C) *Foliage description.*—Small, dark green leaves with a reddish purple midrib. No variegation in the leaf. (1) Size: Mature foliage is 9 to 10 cm long and 2.5 to 3.0 cm wide at the widest point.

(2) Shape: Lanceolate with acuminate apex and acute base. (3) Texture: Slightly rugose upper side, underside glabrous. (4) Margin: Finely serrated with fine cilia. (5) Color: Young foliage top side, 146A. Under side: between 187A-B. Mature foliage top side, 147A. Under side: between 187A-B. (6) Venation: Pinnate, reddish purple in color, especially the midrib.

Flowering description:

(A) *Flowering habits.*—Flowers continuously from leaf whorl in progressively orderly manner, taking 5 to 7 days from bud to bloom. Each leaf axil has two flower buds and the secondary ones do not open until all primary flowers in an axial have opened. Before the secondary flowers finish opening, the primary flowers on the whorl above start to open. Flowers last 2 to 3 weeks. Sunregal has the ability to flower under high temperature and light levels.

(B) *Natural flowering season.*—Indeterminant and continuous. Quantity of flowering increases with increasing levels of light.

(C) *Flower buds.*—Ellipsoidal, flowers perfect, red spur 2.5 to 3.0 cm long on mature buds; throat behind ovary and originating from the major sepal.

(D) *Flowers borne.*—On individual short 4 cm pedicels at maturity from a whorl of 4 to 5 leaves; flowering progressively around the whorl with all primary flowers in a whorl opening before the secondary ones start to open.

(E) *Quantity of flowers.*—Very floriferous due to the two flower buds per leaf axil; flowering development is continuous so that tight buds and mature flowers are present at the same time.

(F) *Petals.*—(1) Shape: Heart shaped with upper petal dominant in size.

(2) *Color.*—Top side in summer when opening for the upper petal, the midrib area and the inner $\frac{1}{4}$ area of the other 4 petals is slightly lighter than 74B red purple and fades somewhat to between 74B and 74C. The other areas of the 4 lower petals (outer lobe area) open at 69A Red Purple and fade to 69B. The extreme inner part of the petal and the midrib area of the upper petals are 45A Red Group. (3) Number of petals: Five (5) in number. (4) Size of flowers: 5 to 6 cm in diameter.

(G) *Reproductive organs.*—(1) Stamens: Five (5) in number. (a) Anther shape: Hooded, color cream. (b) Pollen color: Cream. (2) Pistels: (a) Stigma: Five (5) in number, segmented column shaped; color, purple tinted. (b) Style color: Purple tinted. (c) Ovaries: Five (5) in number, celled, 5 mm until fertilized, dark green with purple tint.

Disease resistance: No significant disease problem noted to date.

I claim:

1. A new and distinct cultivar of Impatiens plant named Sunregal, as described and illustrated, and particularly characterized by its lavender purple bicolor flowers; deep red-purple main stem; compact self-branching growth habit; small dark green and shiny leaves with a purple midrib, and by its ability to produce two flowers per each leaf axil thereby making it highly floriferous.

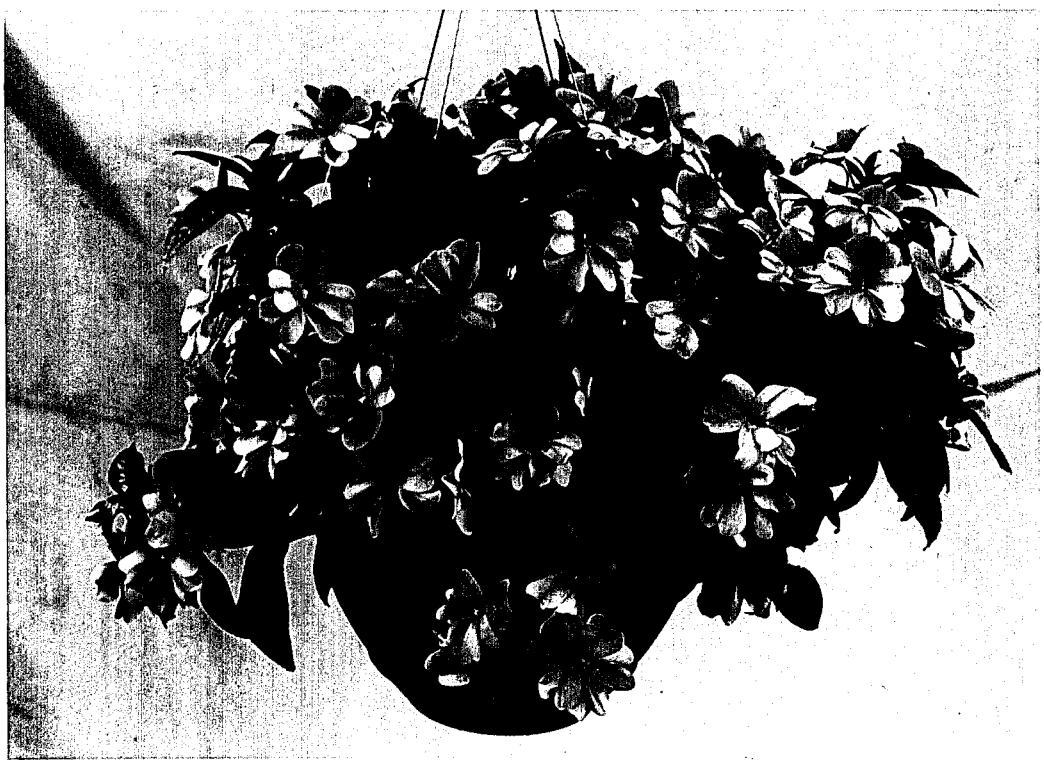

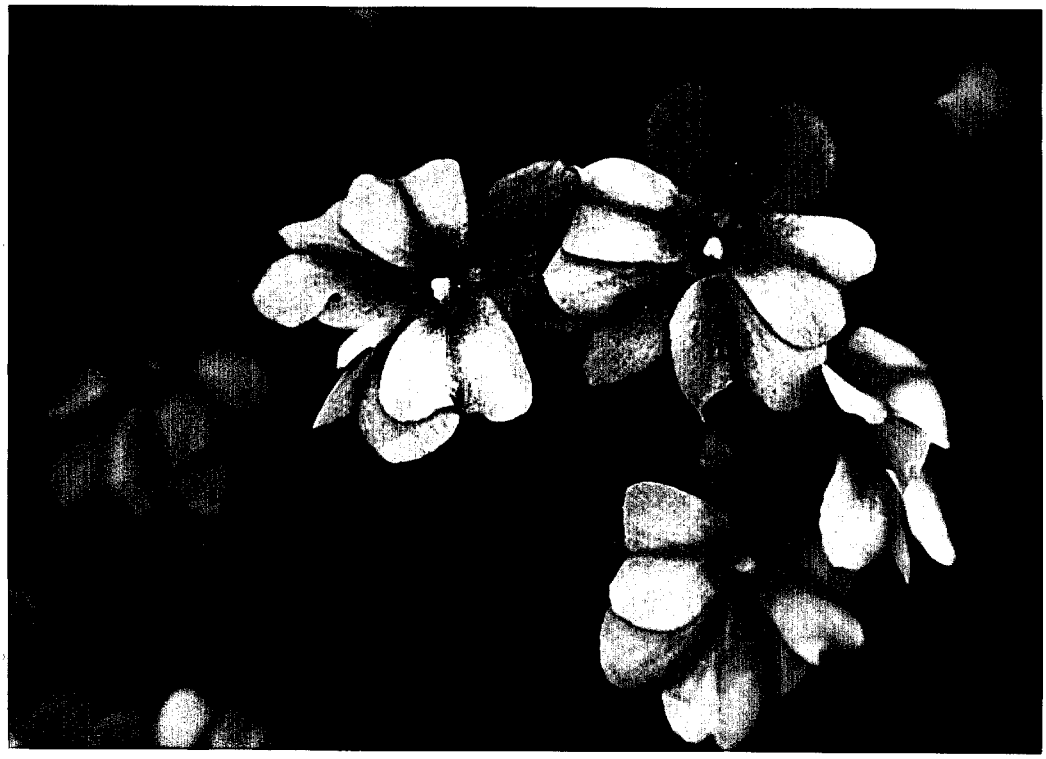

* * * * *